United States Patent [19]
Dubrow

[11] Patent Number: 5,948,227
[45] Date of Patent: Sep. 7, 1999

[54] METHODS AND SYSTEMS FOR PERFORMING ELECTROPHORETIC MOLECULAR SEPARATIONS

[75] Inventor: Robert S. Dubrow, San Carlos, Calif.

[73] Assignee: Caliper Technologies Corp., Mountain View, Calif.

[21] Appl. No.: 08/992,239

[22] Filed: Dec. 17, 1997

[51] Int. Cl.$^6$ .................................................. B01D 57/02
[52] U.S. Cl. ........................ 204/455; 204/454; 204/605
[58] Field of Search .................................. 204/451–455, 204/601–605; 435/6, 287.2, 288.5; 422/68.1, 70, 101; 436/86, 89, 90, 94; 210/656, 658, 198.2, 198.3

[56] References Cited

U.S. PATENT DOCUMENTS

| | | |
|---|---|---|
| 4,390,403 | 6/1983 | Batchelder . |
| 4,908,112 | 3/1990 | Pace . |
| 5,089,111 | 2/1992 | Zhu et al. . |
| 5,110,424 | 5/1992 | Chin . |
| 5,126,021 | 6/1992 | Grossman . |
| 5,126,022 | 6/1992 | Soane et al. . |
| 5,171,534 | 12/1992 | Smith et al. . |
| 5,181,999 | 1/1993 | Wiktorowicz . |
| 5,264,101 | 11/1993 | Demorest et al. . |
| 5,332,481 | 7/1994 | Guttman . |
| 5,374,527 | 12/1994 | Grossman . |
| 5,498,392 | 3/1996 | Wilding et al. . |
| 5,552,028 | 9/1996 | Madabhushi et al. . |
| 5,567,292 | 10/1996 | Madabhushi et al. . |
| 5,571,410 | 11/1996 | Swedberg et al. . |
| 5,585,069 | 12/1996 | Zanzucchi et al. . |
| 5,593,838 | 1/1997 | Zanzucchi et al. . |
| 5,603,351 | 2/1997 | Cherukuri et al. . |
| 5,635,358 | 6/1997 | Wilding et al. . |
| 5,637,469 | 6/1997 | Wilding et al. . |

FOREIGN PATENT DOCUMENTS

| | | |
|---|---|---|
| 0 665 430 | 8/1995 | European Pat. Off. . |
| WO 96/04547 | 2/1996 | WIPO . |
| WO 97/02357 | 1/1997 | WIPO . |

OTHER PUBLICATIONS

Dasgupta, P.K. et al., "Electroosmosis: A Reliable fluid Propulsion System for Flow Injection Analysis," *Anal. Chem.* 66:1792–1798 (1994).

Jacobson, S.C. et al., "Fused Quartz Substrates for Microchip Electrophoresis," *Anal. Chem.* 67:2059–2063 (1995).

Manz, A. et al., "Electroosmotic pumpgin and electrophoretic separations for miniaturized chemical analysis systems," *J. Micromech. Microeng.* 4:257–265 (1994).

Ramsey, J.M. et al., "Microfabricated chemical measurement systems," *Nature Med.* 1:1093–1096 (1995).

Seiler, K. et al., "Planar Glass Chip for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid flow within a Manifold of Capillaries on a Glass Chip," *Anal. Chem.* 66:3485–3491 (1994).

*Primary Examiner*—William H. Beisner
*Attorney, Agent, or Firm*—Matthew B. Murphy

[57] ABSTRACT

The present invention provides methods of electrophoretically separating macromolecular species, as well as compositions and systems useful in carrying out such methods. Specifically, the methods of the present invention comprise providing a substrate that has at least a first capillary channel disposed therein. The surface of the channel has a first surface charge associated therewith, and is filled with a water soluble surface adsorbing polymer solution that bears a net charge that is the same as the charge on the capillary surface.

50 Claims, 9 Drawing Sheets

METHODS AND SYSTEMS FOR PERFORMING ELECTROPHORETIC MOLECULAR SEPARATIONS

BACKGROUND OF THE INVENTION

Capillary electrophoresis has been established as a highly effective method for separating macromolecular species in order that they might be further characterized. Protein and nucleic acid molecules are two major examples of molecular species that are routinely fractionated and characterized using capillary electrophoretic systems. These systems have generally proven effective as a result of the high surface to volume ratio of the thin capillaries. This high surface to volume ratio allows for much greater heat dissipation, which in turn, allows application of greater electrical currents to the capillary thereby resulting in a much more rapid separation of macromolecules introduced into the system.

In the capillary electrophoretic, size-based separation of biological macromolecules of interest, e.g., proteins and nucleic acids, electrophoretic separation is not possible in a free solution. Instead, such separation requires the presence of a matrix that alters the electrophoretic mobilities of these molecules based upon their relative size.

Although early capillary electrophoresis systems utilized solid gel matrices, e.g., cross-linked polyacrylamides, more recent systems have employed liquid polymer solutions as a flowable matrix, which permits adequate separation efficiencies without the drawbacks of cross-linked capillary systems, i.e., in introducing such matrices to or removing them from capillary channels.

For example, U.S. Pat. No. 5,126,021 reports a capillary electrophoresis element which includes a capillary electrophoresis tube containing a low viscosity uncharged polymer solution, for separating nucleic acids.

U.S. Pat. No. 5,264,101 to Demorest et al. reports the use of a hydrophilic polymer solution, which is characterized by a molecular weight of 20 to 5,000 Kd, and a charge between 0.01 and 1% as measured by the molar percent of total monomer subunits to total polymer subunits, where the charge is opposite to the charge of the surface of the capillary in which the polymer is used. This opposite charge of the polymer is reported to result in an interaction between the polymer and the capillary wall to reduce electroosmotic flow within the capillary.

U.S. Pat. Nos. 5,552,028 and 5,567,292, both to Madabhushi et al., report the use of a uncharged, water soluble, silica adsorbing polymer in a capillary electrophoresis system to reduce or eliminate electroosmotic flow.

Surprisingly, the present inventor has discovered that polymer solutions can be used in capillary channel systems, which polymers employ a charge that is the same as that of the internal capillary surface, e.g., positive or negative. Even more surprisingly, it has been discovered that electroosmotic flow in capillary channel systems containing such polymer solutions is maintained the same level or lower than with an uncharged polymer solution. The present invention provides such polymers, as well as methods of utilizing these polymers and systems employing such polymers.

SUMMARY OF THE INVENTION

The present invention generally provides novel methods and compositions for use in the separation of molecular, and particularly macromolecular species by electrophoretic means.

For example, in an aspect of the present invention is provided a method of separating macromolecules by capillary electrophoresis. The method generally comprises providing a substrate which includes at least a first capillary channel disposed therein, where a surface of the channel has a first surface charge associated therewith. The capillary channel is filled with a water soluble hydrophilic polymer solution which includes a percent charge of from about 0.01% to about 2%, as calculated by the molar percent of charged monomer subunits to total monomer utilized in producing the polymer. The charged monomer subunits have a charge that is the same as the first surface charge. A sample containing macromolecules is introduced into one end of the capillary channel and a voltage gradient is applied across the length of the capillary channel, whereby the macromolecules in the sample are separated in the capillary channel. In preferred aspects, the surface charge of the capillary channel, as well as the charged monomer subunits bear a negative charge. In further preferred aspects, the capillary channel is disposed within a silica substrate.

In a related aspect, the present invention also provides systems and apparatus for practicing the above methods. In particular, the present invention provides a system for separating macromolecules by capillary electrophoresis. The system comprises a substrate having at least a first walled capillary channel disposed therein, where the channel includes a net surface charge associated with its interior surfaces. A solution of silica adsorbing polymer as described above, is disposed in the capillary channel. The system also includes a power source electrically coupled to the capillary channel for applying a voltage gradient across the capillary channel.

DETAILED DESCRIPTION OF THE INVENTION

Figure 1:
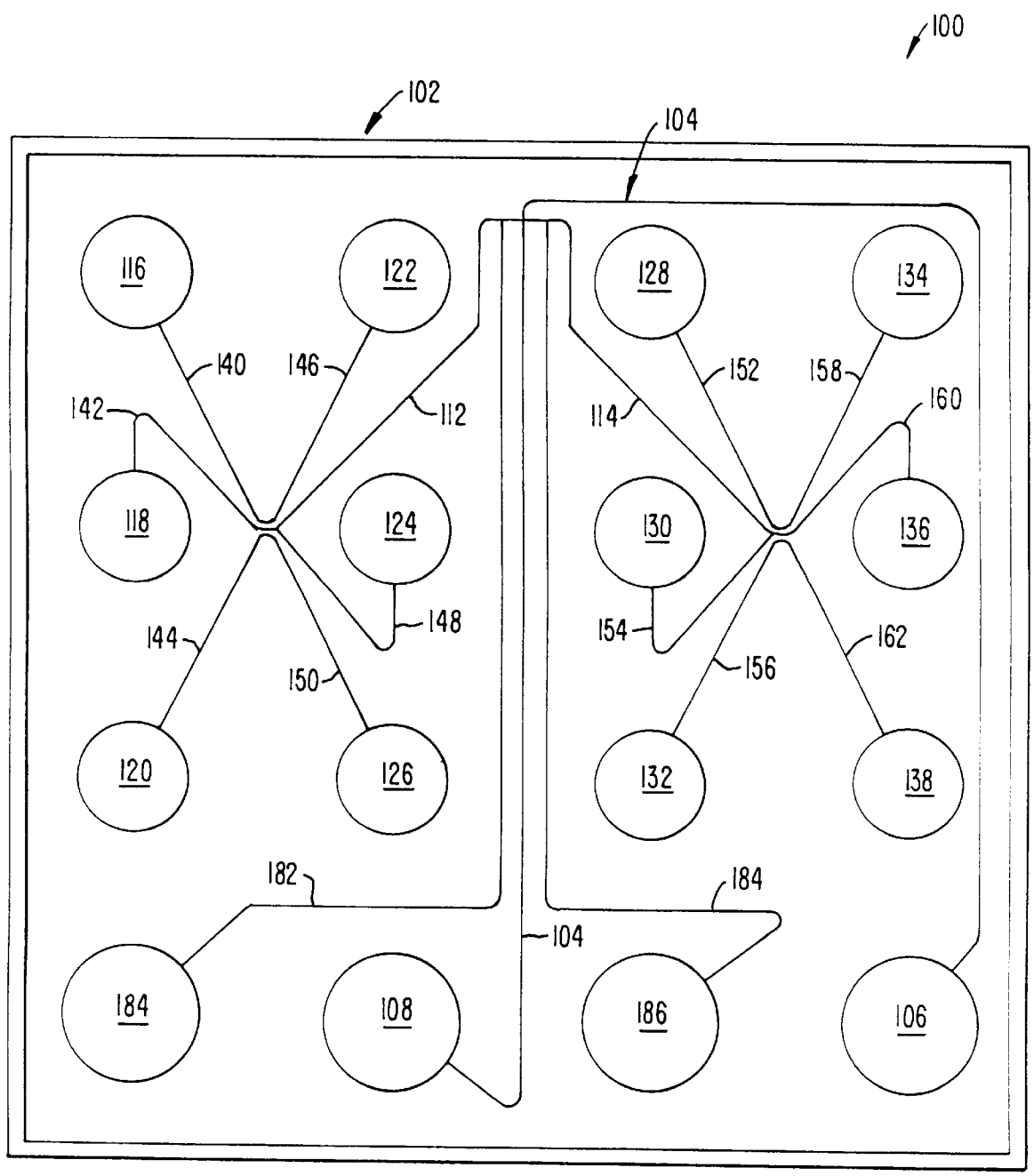
FIG. 1 schematically illustrates a silica microscale electrophoresis device for use in electrophoretic separation of sample component for up to 12 different sample materials, in accordance with the present invention.
Figure 2A:
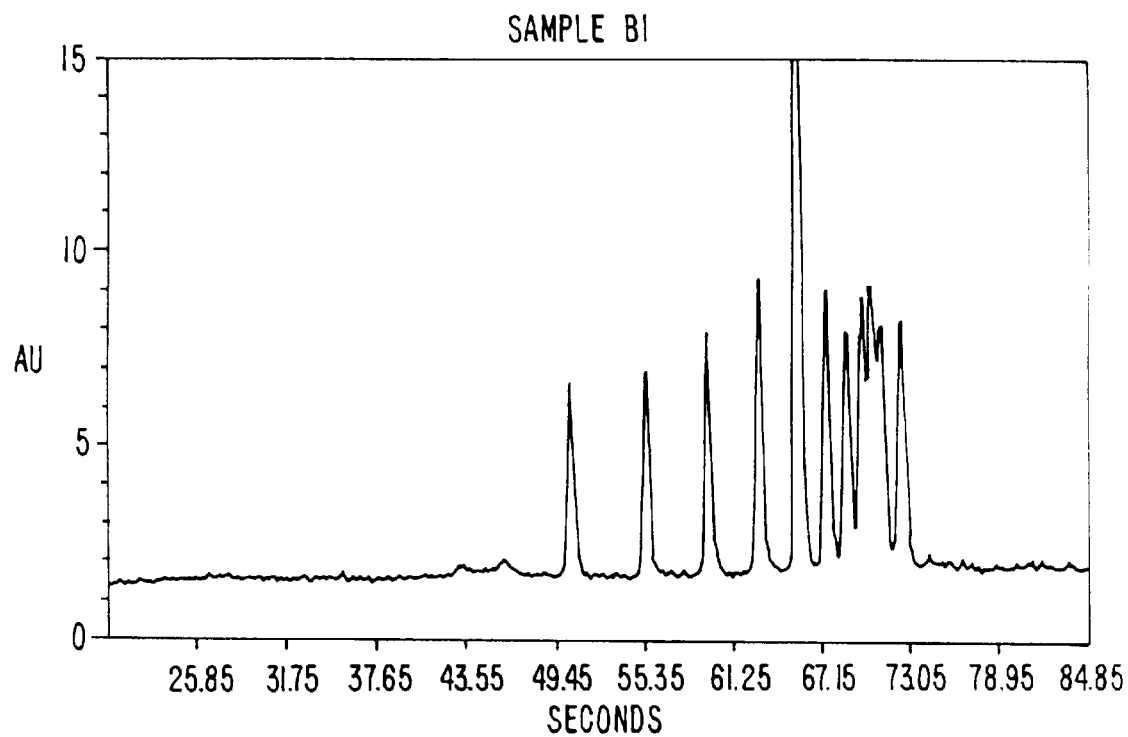
FIGS. 2A–2D illustrate the chromatographic separation of DNA standard samples in a silica microscale integrated channel electrophoresis device first filled with a neutral polymer solution.
Figure 2B:
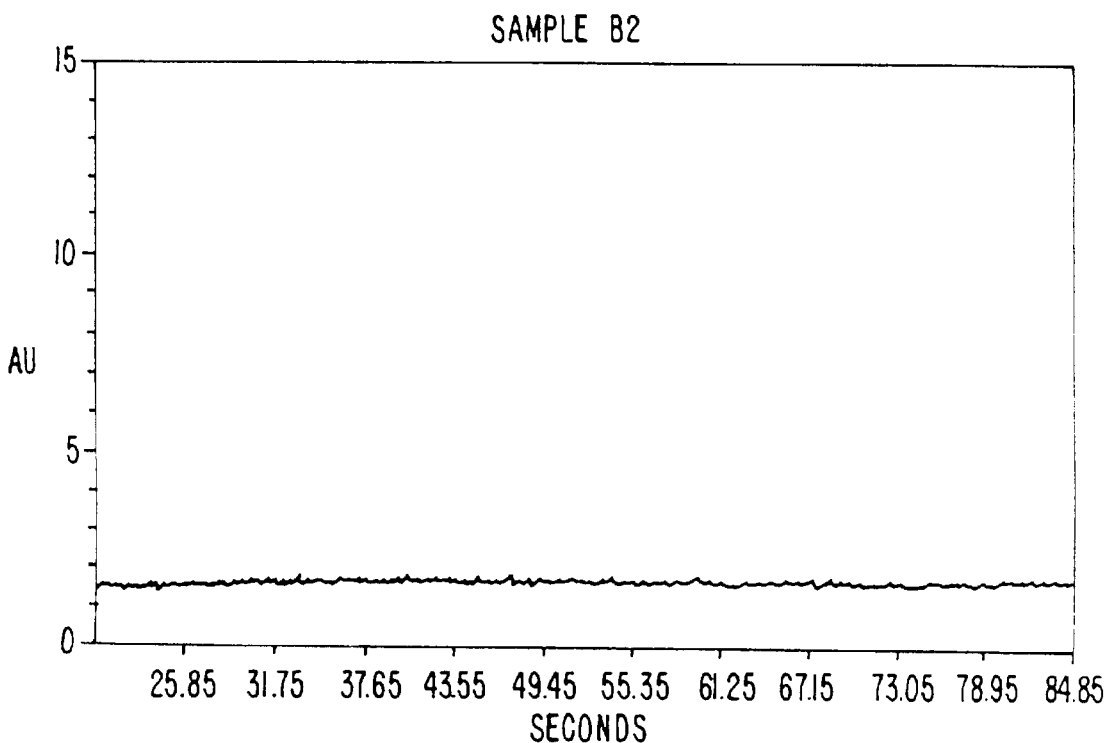
Figure 2C:
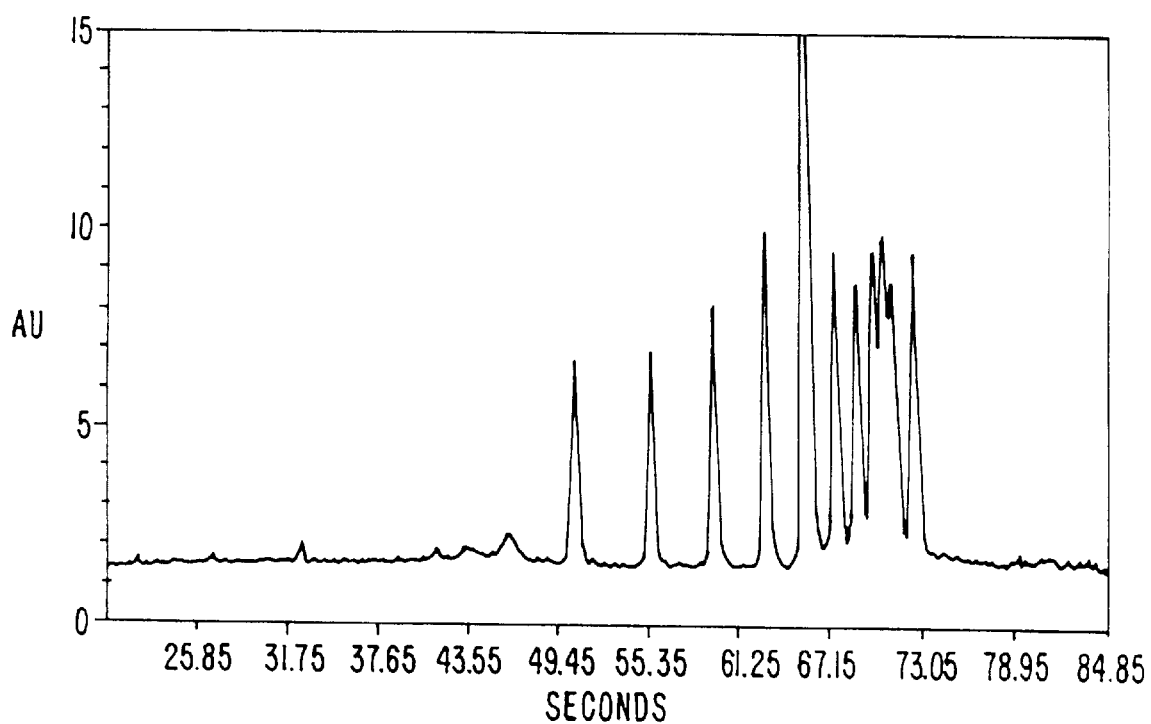
Figure 2D:
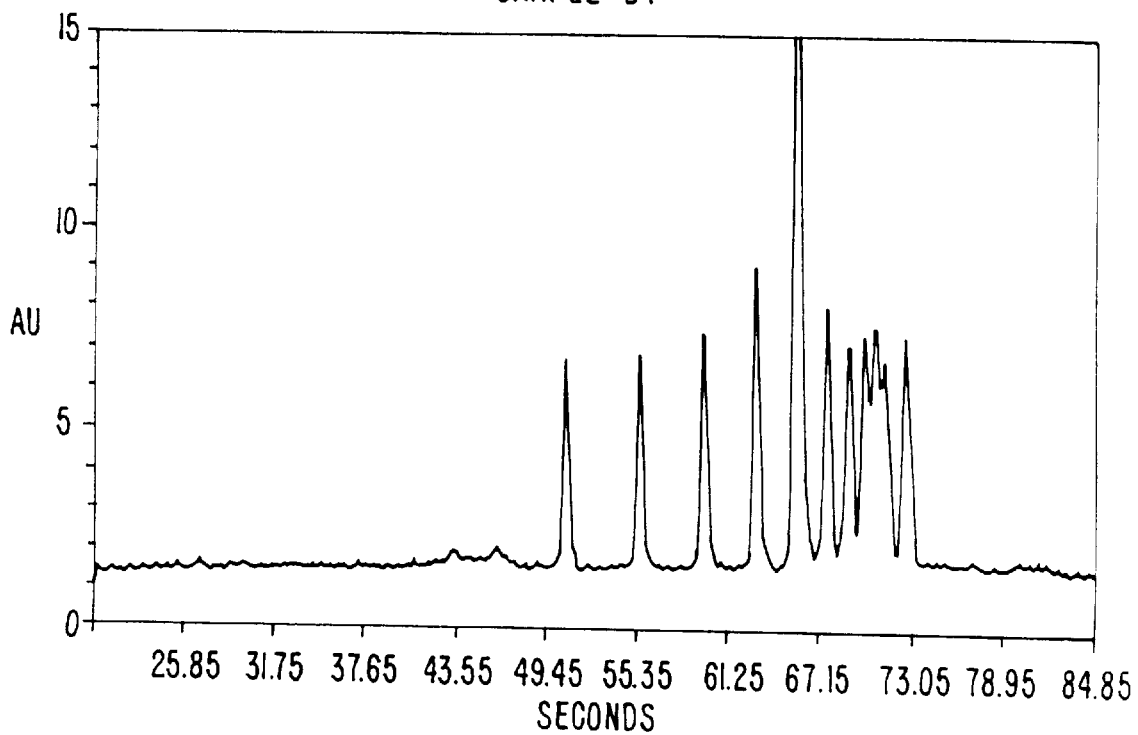
Figure 3A:
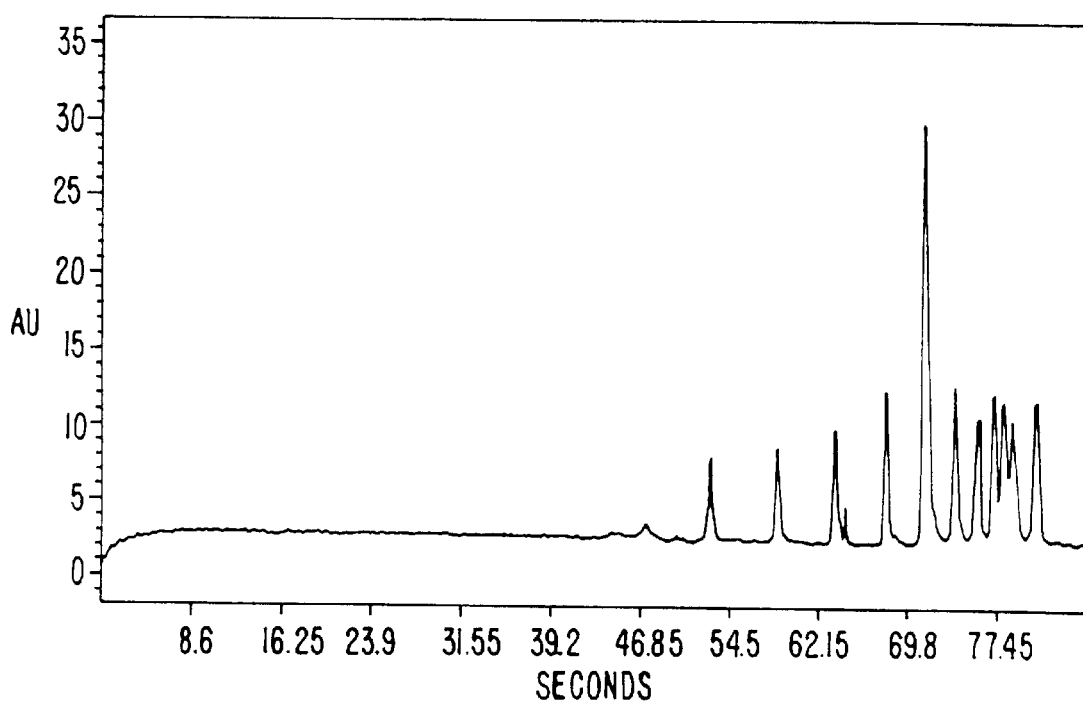
FIGS. 3A–3D illustrate the chromatographic separation of DNA standard samples in a silica microscale integrated electrophoresis device first filled with a polymer solution having a negative charge associated with it.
Figure 3B:
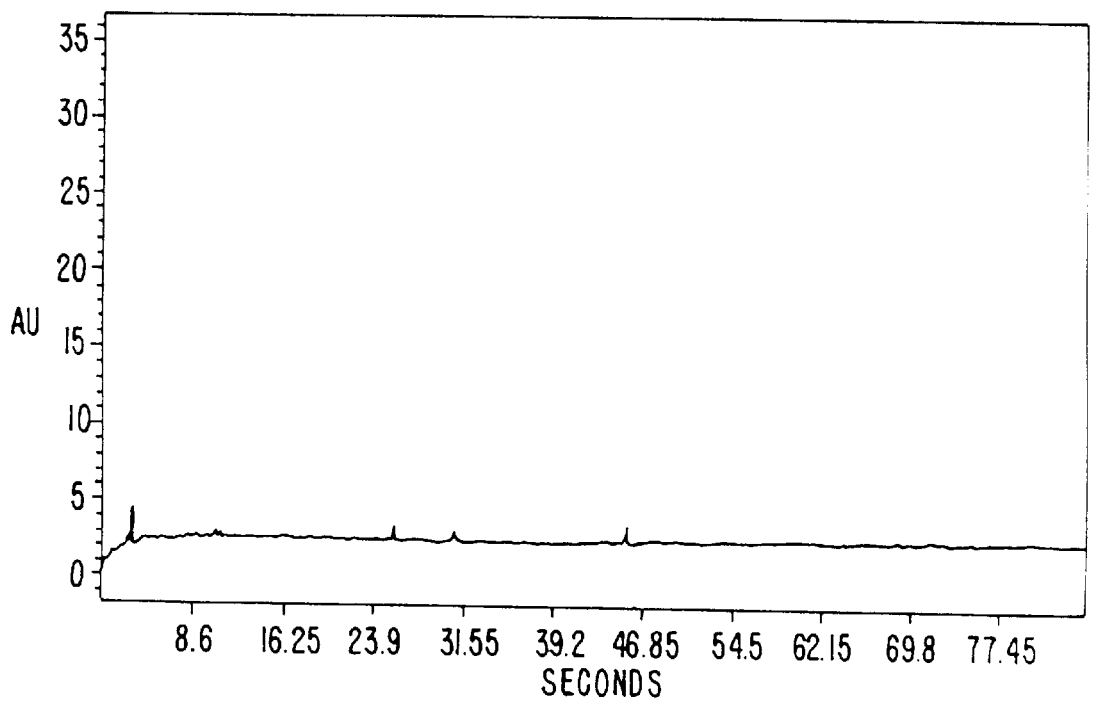
Figure 3C:
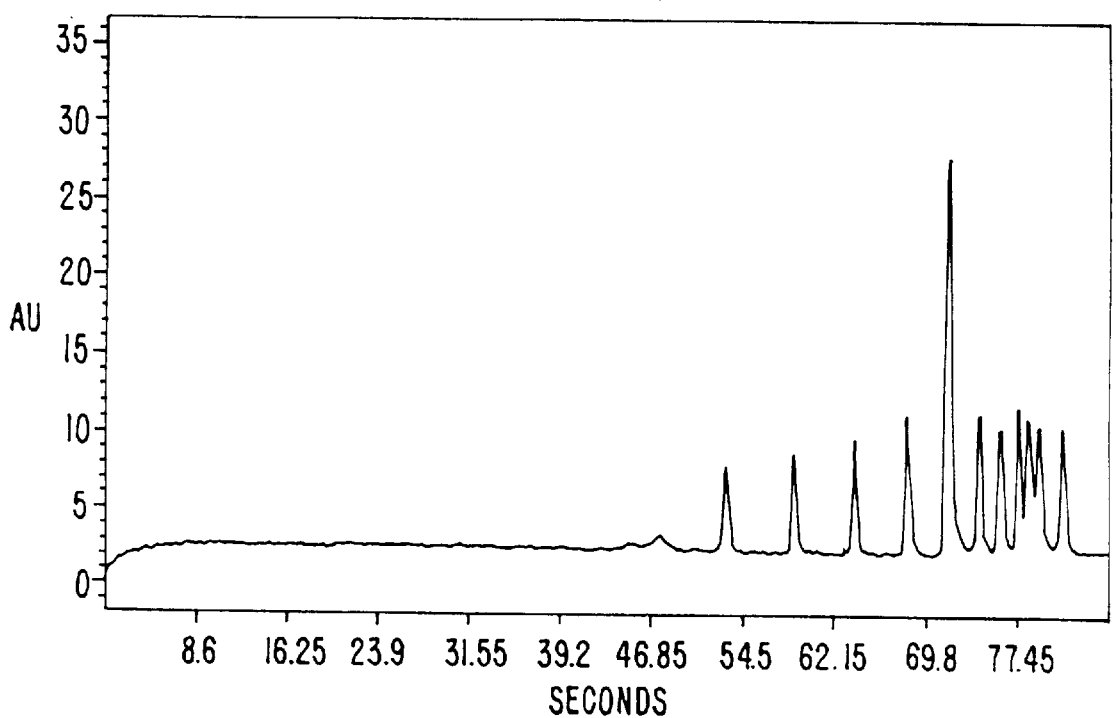
Figure 3D:
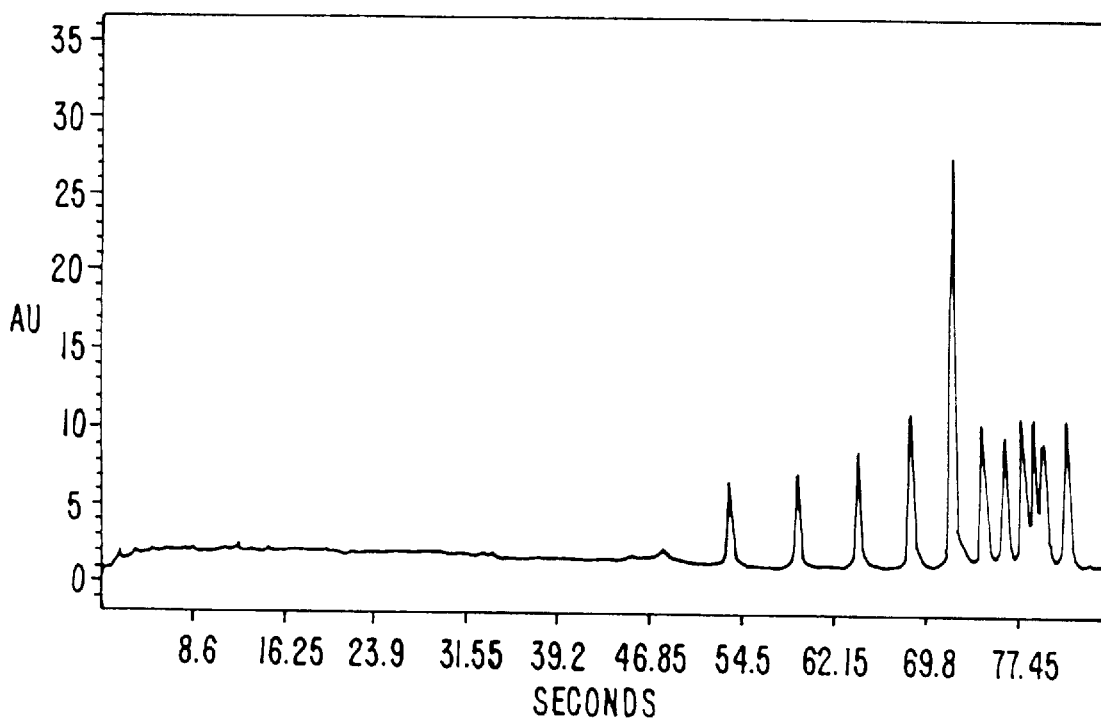

The present invention provides methods of electrophoretically separating macromolecular species, as well as compositions and systems useful in carrying out such methods.

Specifically, the methods of the present invention comprise providing a substrate that has at least a first capillary channel disposed therein. The surface of the channel has a first surface charge associated therewith, and is filled with a water soluble surface adsorbing polymer solution that bears a net charge that is similar to or the same as the charge on the capillary surface, e.g., positive or negative.

As used herein, the term substrate typically refers to a solid substrate in which a capillary channel is disposed. Exemplary substrates include silica based substrates, such as silica, e.g., glass, quartz or the like, silicon, etc., polymeric substrates, e.g., plastics like polydimethylsiloxanes (PDMS), polymethylmethacrylate (PMMA), polyurethane, polyvinylchloride (PVC), polystyrene, polysulfone, polycarbonate, polytetrafluoroethylene (Teflon™), and a variety of others that are well known in the art. Substrates may take a variety of shapes or forms, including tubular substrates, e.g., polymer or fused silica capillaries, or the like. In preferred aspects, however, the substrate comprises a planar body structure in which grooves are fabricated to define capillary channels when overlaid with a cover element, also typically planar in structure. Examples of such planar capillary systems are described in commonly assigned copending U.S. application Ser. No. 08/845,754, filed Apr. 25, 1997 and incorporated herein by reference.

Capillary channels also can be any of a variety of different shapes in cross-section, including tubular channels, rectangular channels, rhomboid channels, hemispherical channels or the like, or even more arbitrary shapes, such as may result from less precise fabrication techniques, e.g., laser ablation. Typically, the shape of a capillary channel will vary depending upon the substrate type used and the method of fabrication. For example, in typical fused silica capillaries, the capillary channel will be tubular. In systems employing planar substrates, on the other hand, channels will typically comprise either a rhomboid, rectangular or hemispherical cross sectional shape, depending upon the substrate material and method of fabrication of the channels.

A variety of manufacturing techniques are well known in the art for producing microfabricated channel systems. For example, where such devices utilize substrates commonly found in the semiconductor industry, manufacturing methods regularly employed in those industries are readily applicable, e.g., photolithography, wet chemical etching, chemical vapor deposition, sputtering, electroforming, etc. Similarly, methods of fabricating such devices in polymeric substrates are also readily available, including injection molding, embossing, laser ablation, LIGA techniques and the like. Other useful fabrication techniques include lamination or layering techniques, used to provide intermediate microscale structures to define elements of a particular microscale device.

Typically, the capillary channels will have an internal cross-sectional dimension, e.g., width, depth, or diameter, of between about 1 $\mu$m and about 500 $\mu$m, with most such channels having a cross-sectional dimension in the range of from about 10 $\mu$m to about 200 $\mu$m.

In particularly preferred aspects, planar microfabricated devices employing multiple integrated microscale capillary channels are used. Briefly, these planar microscale devices employ an integrated channel network fabricated into the surface of a planar substrate. A second substrate is overlaid on the surface of the first to cover and seal the channels, and thereby define the capillary channels.

One or more analysis channels are provided in the device with additional channels connecting the analysis channel to multiple different sample reservoirs. These reservoirs are generally defined by apertures disposed in the second overlaying substrate, and positioned such that they are in fluid communication with the channels of the device. A variety of specific channel geometries are employed to optimize channel layout in terms of material transport time, channel lengths and substrate use. Examples of such microscale channel network systems are described in detail in U.S. application Ser. Nos. 60/060,902, filed Oct. 3, 1997, and incorporated herein by reference in its entirety. One specific example of a channel geometry is illustrated in FIG. 1. In operation, sample materials are placed into one or more of the sample reservoirs 116–138. A first sample material, e.g., disposed in reservoir 116, is then loaded by electrokinetically transporting it through channels 140 and 112, and across the intersection with the separation channel 104, toward load/waste reservoir 186 through channel 184. Sample is then injected by directing electrokinetic flow from buffer reservoir 106 through analysis channel 104 to waste reservoir 108, while pulling back the sample in the loading channels 112:114 at the intersection. While the first sample is being separated in analysis channel 104, a second sample, e.g., that disposed in reservoir 118, is preloaded by electrokinetically transporting it into channels 142 and 112 and toward the load/waste reservoir 184 through channel 182. After separation of the first sample, the second sample is then loaded across the intersection with analysis channel 104 by transporting the material toward load/waste reservoir 186 through channel 184.

The interior surface of the capillary channels typically has a charge associated with it. For example, in the case of capillary channels disposed in silica-based substrates, e.g., glass or quartz, the interior surface of the channel typically includes negatively charged chemical groups, e.g., silane groups, associated with it. Similarly, polymeric substrates also typically comprise some level of charged chemical groups at their surface, although at much lower level than in the case of silica-based substrates. As used herein, a "charged surface" of a capillary is typically characterized by its ability to support an electroosmotic mobility of a fluid or material in the channel. In particular, channels having charged surfaces as described herein, are typically capable of supporting an electroosmotic mobility ($\mu$EO) of at least about $1\times10^{-5}$ cm$^2$V$^{-1}$s$^{-1}$, for a buffer when that buffer is in contact with those walls, e.g., disposed within those channels, e.g., a buffer of from about 1 mM to about 100 mM sodium borate at a pH of from about 6 to about 9. For the purposes of the present invention, $\mu$EO is defined in terms of a standard buffer of from about 1 mM to about 10 mM sodium borate buffer, at a pH of from about 7 to about 9, for example, 5 mM sodium borate, pH 7. In more common aspects, the charged surfaces in contact with the fluid are capable of supporting a $\mu$EO under the above conditions, of at least about $2\times10^{-5}$ cm$^2$V$^{-1}$s$^{-1}$, preferably, at least about $5\times10^{-5}$cm$^2$V$^{-1}$s$^{-1}$, and in particularly preferred aspects, at least about $1\times10^{-6}$ cm$^2$V$^{-1}$s$^{-1}$.

Different surfaces can also be treated to present differing levels or types of charged groups. Examples of such surface treatments are described in detail in copending, commonly assigned U.S. application Ser. No. 08/843,212, filed Apr. 14, 1997, now U.S. Pat. No. 5,885,470, and incorporated herein by reference in its entirety for all purposes. In particularly preferred aspects of the present invention, capillary channels disposed in silica substrates are used, e.g., planar silica substrates or fused silica capillaries.

In aqueous systems, when charged capillary surfaces are combined with electric fields necessary for electrophoretic separation, electroosmotic flow results. For many separations, e.g., protein separations, some electroosmotic flow is actually desired, in order to ensure a net movement of all proteins through a capillary channel and past a detector. However, it is generally desirable to be able to precisely control that level of flow. In the capillary electrophoretic separation of nucleic acids on the other hand, it is generally desirable to suppress electroosmotic flow entirely, to enhance resolution of separation. Further, such charged surfaces have been implicated in the binding of components of samples, e.g., proteins, etc., which binding has been blamed for reduced efficiency of separation.

In accordance with the methods of the present invention, the above described capillary channel or channels are filled with a solution of a water-soluble silica-adsorbing polymer. The polymer typically includes a percent charge of between about 0.01% and 2% that is the same as the charge that is associated with the interior wall surface of the capillary channel. By "a charge that is the same as the charge of the interior surface of the capillary channel" is meant that the polymer includes charged monomer subunits that are the same charge, e.g., negative or positive, as the charged chemical groups on the interior surface of the capillary channel. Thus, where a capillary channel includes negatively charged groups on the interior surface, e.g., silane groups in silica capillary channels, the polymer will include monomer subunits that are negatively charged. In accordance with the present invention, the polymer will preferably not include any charged monomer subunits that have a charge opposite to the charge on the interior surface of the capillary channel. In preferred aspects, the polymer has a percent charge of between about 0.01% and about 1%, more preferably, between about 0.01% and about 0.5%, and still more preferably between about 0.05% and 0.5%, and often between about 0.05% and 0.2%. As noted above, in preferred aspects, the present invention utilizes silica based substrates, e.g., planar substrates or capillaries. As such, also in preferred aspects, the polymers used in accordance with the invention are negatively charged, as is the interior surface of the capillary channel.

As used herein, the "percent charge" of a polymer refers to the molar percent of charged monomer units to total monomer subunits used in the synthesis of the polymer. Thus, if the synthesis reaction is carried out by mixing 1 mmol of charged subunit and 99 mmol of uncharged monomer subunit, the polymer would have a percent charge of 1%, as defined herein.

The water soluble polymers of the present invention are preferably surface adsorbing polymers, and more preferably, silica adsorbing polymers, e.g., as that term is defined in U.S. Pat. No. 5,567,292, incorporated herein by reference in its entirety for all purposes. Examples of particularly preferred surface adsorbing polymers include acrylic polymers, e.g., polyacrylamides, polymethylacrylamides, polydimethylacrylamides, and the like. Each of these polymers is readily synthesized to incorporate charged monomer subunits bearing a charge that is the same as the charge of the interior surface of the capillaries, e.g., negatively charged subunits. For example, carboxylic acid monomers can be used to impart a negative charge to the polymer. Such monomers include, e.g., acrylic acid, bisacrylamidoacetic acid, 4,4-Bis(4-hydroxyphenyl)pentanoic acid, 3-butene-1,2,3-tricarboxylic acid, 2-carboxyethylacrylate, itaconic acid, methacrylic acid, 4-vinylbenzoic acid, and others. Sulfonic acid or phosphoric acid monomers may also be used to impart negative charge, including, e.g., 2-acrylamido-2-methyl-1-propanesulfonic acid, 2-methyl-2-propene-1-sulfonic acid, 2-propene-1-sulfonic acid, 4-styrenesulfonic acid, 2-sulfoethyl methacrylate, 3-sulfopropyldimethyl-3-methacrylamidopropylammonium inner salt, 3-sulfopropyl methacrylate, vinylsulfonic acid, Bis(2-methacryloxyethyl) phosphate, monoacryloxyethyl phosphate, and others. In the case of systems employing capillary channels with positively charged surfaces, positively charged monomer units are substituted. A variety of such subunits are known to those of skill in the art, and include, for example, quaternary amine monomers, such as 2-acryloxyethyltrimethylammonium chloride, diallyldimethylammonium chloride, 2-methacryloxyethyltrimethylammonium chloride, 3-methacryloxy-2-hydroxypropyltrimethylammonium chloride, and others.

In particularly preferred aspects, the surface adsorbing polymer is a polydimethylacrylamide polymer-co-acrylic acid. In this case, the polymer is a dimethylacrylamide polymer incorporating a desired percentage of charged acrylic acid monomers, as described above.

Synthesis of polymers used in the methods of the present invention may be carried out by any number of methods that are well known in the art. Typically, synthesis conditions and protocols will vary depending upon the polymer to be synthesized and the nature and amount of charge to be incorporated. Examples of suitable polymer synthesis methods are described in, e.g., Odian, Principles of Polymerization, Third Ed. (John Wiley, New York, 1991), and U.S. Pat. Nos. 5,264,101 and 5,567,292, all of which are incorporated herein by reference.

For use, the polymer may be provided in an aqueous solution at a concentration between about 0.01% and 30% (w/v). Different concentrations may be used depending upon the nature of the separation to be performed, the size of the capillary channel and the like. Preferably, the polymer concentration, as used in the separation methods described herein, is between about 0.01% and about 20% (w/v), and more preferably, between about 0.1% and about 10%.

The average molecular weight of the polymer within the polymer solutions may vary somewhat depending upon the application for which the polymer solution is desired. For example, applications which require higher resolution, e.g., single base resolution in sequencing applications, may utilize higher molecular weight polymer solutions, while less stringent applications can utilize lower molecular weight polymer solutions. Typically, the polymer solutions used in accordance with the present invention have an average molecular weight in the range of from about 1 Kd to about 6,000 Kd, preferably between about 1 Kd and about 1000 Kd, and more preferably, between about 100 kD and about 1000 Kd.

In addition to the percent charge and molecular weights described above, the polymers used in accordance with the present invention are also characterized by their viscosity. In particular, the polymer components of the system described herein typically have a solution viscosity as used within the capillary channel, in the range of from about 2 to about 1000 centipoise, preferably, from about 5 to about 200 centipoise and more preferably, from about 10 to about 100 centipoise.

In addition to the polymer component, the polymer solution typically includes buffers for controlling pH and conductivity, other polymers and the like, as necessary for accomplishing the desired separation, i.e., neutral polymers for enhancing sieving, and the like.

In operation, a solution of the water-soluble surface-adsorbing polymer is introduced into the capillary channel.

This introduction may be as simple as placing one end of the channel into contact with the polymer solution and allowing the polymer to wick into the channel. Alternatively, vacuum or pressure may be used to drive the polymer solution into the capillary channel. In the preferred integrated channel systems, the polymer solution is typically placed into contact with a terminus of a common capillary channel, e.g., a reservoir disposed at the end of a separation channel, and slight pressure is applied to force the polymer into all of the integrated channels.

The sample containing the macromolecular species for which separation is desired, is placed in one end of the separation channel and a voltage gradient is applied along the length of the channel. As the sample components are electrokinetically transported down the length of the channel and through the polymer solution disposed therein, those components are resolved. The separated components are then detected at a point along the length of the channel, typically near the terminus of the separation channel distal to the point at which the sample was introduced.

Detection of separated species is typically carried out using UV, amperometric and/or fluorescent detection systems that are well known in the art. Typically, such detection systems operate by detecting a characteristic optical property of the macromolecular species of interest, e.g., UV absorbance of double bonded structures, fluorescence of an associated labeling moiety, light scattering, etc. For example, in the case of fluorescent detection, such detection systems typically employ a fluorescent or fluorogenic-labeling group coupled to the various macromolecules. For instance, in the case of nucleic acids, a variety of fluorescent labeling techniques can be used. These are generally well known in the art, and include the use of covalently attached fluorescent labeling groups, e.g., as described in U.S. Pat. Nos. 4,711,955, 5,171,534, 5,187,085, 5,188,934, and 5,366,860, all of which are hereby incorporated herein by reference in their entirety for all purposes. Alternatively, associative labeling groups may be used, which preferentially associate with the macromolecular species of interest, or are only detectable, e.g., fluorescent or fluorogenic, when associated with the macromolecules of interest. Examples of such labeling groups include, e.g., intercalating dyes for double stranded nucleic acids, streptavidin/biotin labeling groups.

As noted, preferred aspects of the present invention utilize fluorescent detection systems. Typically, such systems utilize a light source capable of directing light energy at the separation channel as the separated macromolecular species are transported past. The light source typically produces light of an appropriate wavelength to activate the labeling group. Fluoresced light from the labeling group is then collected by appropriate optics, e.g., an objective lens, located adjacent the capillary channel, and the collected light is directed at a photometric detector, such as a photodiode or photomultiplier tube. The detector is typically coupled to a computer, which receives the data from the detector and records that data for subsequent storage and analysis.

The polymer compositions are widely applicable in the separation of macromolecular species using electrophoretic techniques. Such macromolecular species include without limitation, nucleic acids, proteins, peptides, carbohydrates, and the like. In particularly preferred aspects, the polymer compositions described herein are used in the electrophoretic separation and/or identification of nucleic acids in a sample. Such nucleic acids may include fragments or portions of genomic DNA, e.g., for genotyping, fragments or portions of mRNA, e.g., for gene expression analysis, or polymerization reaction products for verification of amplification processes. In addition, such polymer compositions are particularly useful in separating nested sets of nucleic acid fragments or synthesis products, for determination of nucleotide sequence, e.g., as prepared in Sanger or Maxam and Gilbert sequencing operations. In these sequencing operations, the nested sets of fragments typically include a number of fragments of a target nucleic acid sequence that differ in length from the next fragment by a single nucleotide, e.g., a single base extension. The fragments in these nested sets are then separated by size in, e.g., capillary electrophoretic operations, and characterized by their terminal nucleotides. Analysis of all of the nested fragments then provides the nucleotide sequence of the target sequence. Examples of preferred sequencing operations are described in, e.g., U.S. Pat. No. 5,171,534, previously incorporated by reference, which employ four differentially labeled dideoxynucleotides in a Sanger sequencing operation. Each labeled dideoxynucleotide has a different fluorescent emission or absorption maximum. Random incorporation of each of the four dideoxynucleotides during target template dependent polymerization results in a nested set of fragments including all possible extension products, where each extension product is differentially labeled by virtue of its terminal dideoxynuclotide. The differential labeling permits characterization of the terminal nucleotide in a single detection operation, and subsequent determination of the overall sequence of the target nucleic acid.

The present invention is further illustrated by the following non-limiting examples.

EXAMPLES

I. Polymer Synthesis

Polymer solutions were prepared according to the following protocols:

A. 2-Methyl-1-propanol polymerization of polydimethylacrylamide

To a 25 ml sidearm flask was added 6 ml of 2-methyl-1-propanol and 3 ml of N,N-dimethylacrylamide. The flask was fitted with a one-hole rubber stopper that had an argon gas line feed through the hole to the bottom of the flask. The side arm of the flask was left open. A steady stream of argon was bubbled through the solution in the flask for 10 minutes. After the 10 minute bubbling period was over three milligrams of 2,2' Azobisisobutyronitrile was added to the flask. The flask was lowered into a 60° C. water bath and the bubbling of the argon gas continued. After one hour the flask was allowed to cool to ambient temperature. The solution in the flask was now a viscous liquid indicating that polymerization had occurred. Purification of the polymer was achieved by subjecting it to a series of precipitation's and dissolutions. The polymer was precipitated out in 100 ml of hexane. The hexane was poured off and the polymer precipitate was dissolved in about 50 ml of methylene chloride. This solution was then precipitated out in hexane again and redesolved in methylene chloride. After one final hexane precipitation the purified polymer was vacuum dried for 48 hours. It was then stored in a glass vial labeled Polymer #1.

B. 2-Methyl-1-propanol polymerization of polydimethylacrylamide/acrylic acid (99.9/0.1)

To a 25 ml sidearm flask was added 6 ml of 2-methyl-1-propanol, 3 ml of N,N-dimethylacrylamide and 0.0054 ml of acrylic acid. The flask was fitted with a one-hole rubber stopper that had an argon gas line feed through the hole to the bottom of the flask. The side arm of the flask was left open. A steady stream of argon was bubbled through the solution in the flask for 10 minutes. After the 10 minute bubbling period was over three milligrams of 2,2' Azobisisobutyronitrile was added to the flask. The flask was lowered into a 60° C. water bath and the bubbling of the argon gas continued. After one hour the flask was allowed to cool to ambient temperature. The solution in the flask was now a viscous liquid indicating that polymerization had occurred. Purification of the polymer was achieved by subjecting it to a series of precipitation's and dissolutions. The polymer was precipitated out in 100 ml of hexane. The hexane was poured off and the polymer precipitate was dissolved in about 50 ml of methylene chloride. This solution was then precipitated out in hexane again and redesolved in methylene chloride. After one final hexane precipitation the purified polymer was vacuum dried for 48 hours. It was then stored in a glass vial labeled Polymer #2.

C. Aqueous polymerization of medium molecular weight polydimethylacrylamide/acrylic acid (99.9/0.1)

To a 25 ml sidearm flask was added 4.0 ml of methanol, 5.0 mL of deionized water, 1.0 mL of N,N-dimethylacrylamide and 0.0018 ml of acrylic acid. The flask was fitted with a one-hole rubber stopper that had an argon gas line feed through the hole to the bottom of the flask. The side arm of the flask was left open. A steady stream of argon was bubbled through the solution in the flask for 10 minutes. A 10 percent solution of ammonium persulfate was made in deionized water. After the 10-minute bubbling period was over 200 µl of the ammonium persulfate solution was added to the flask. The flask was lowered into a 50° C. water bath and the bubbling of the argon gas continued. After 45 minutes the flask was allowed to cool to ambient temperature. The solution in the flask was now a viscous liquid indicating that polymerization had occurred. The solution was transferred into 10 Kd dialysis tubing (Spectrum Technologies, part number 132680). The loaded tubing was placed into 1000 ml of deionized water and stirred for 24 hours. The water was replaced with fresh deionized water and stirred for another 24 hours. After this second 24 hours was complete the dialysis bag was removed from the water, and the contents poured out into a plastic tray. The tray containing the polymer solution was placed in a 60° C. oven for 4 hours to dry. The tray was then removed from the oven and the thin clear film of polydimethylacrylamide/acrylic acid (99.9/0.1) was peeled from the tray and placed in a glass vial for storage and labeled Polymer #3.

D. Aqueous polymerization of high molecular weight polydimethylacrylamide/acrylic acid (99.9/0.1)

To a 25 ml sidearm flask was 8.0 ml of deionized water, 2.0 ml of N,N-dimethacrylamide and 0.0018 ml of acrylic acid. The flask was fitted with a one-hole rubber stopper that had an argon gas line feed through the hole to the bottom of the flask. The side arm of the flask was left open. A steady stream of argon was bubbled through the solution in the flask for 10 minutes. A 10% solution of ammonium persulfate was made in deionized water. After the 10-minute bubbling period was over 200 µl of the ammonium persulfate solution was added to the flask. The flask was lowered into a 50° C. water bath and the bubbling of the argon gas continued. After 45 minutes the flask was allowed to cool to ambient temperature. The solution in the flask was now a soft gel-like material indicating that polymerization had occurred. The polymer was diluted with 30 ml of deionized water and then 10 ml of this solution was transferred into 10 Kd dialysis tubing (Spectrum Technologies, part number 132680). The loaded tubing was placed into 1000 ml of deionized water and stirred for 24 hours. The water was replaced with fresh deionized water and stirred for another 24 hours. After this second 24 hours was complete the dialysis bag was removed from the water, and the contents poured out into a plastic tray. The tray containing the polymer solution was placed in a 60° C. oven for 4 hours to dry. The tray was then removed from the oven and the thin clear film of polydimethacrylamide/acrylic acid (99.9/0.1) was peeled from the tray and placed in a glass vial for storage and labeled Polymer #4.

E. Viscosity Measurements of Polymers

The viscosity of the various polymers prepared as above, was measured at 20° C. using an Ubberholde viscometer (Technical Glass Products, Dover N.J.) following the ASTM D445 test method. Each polymer was mixed with water to the concentration (weight/volume) at which it was used for the electrophoretic separations in the following examples. Viscosities are provided in Table I, below:

TABLE I

| Polymer | Concentration (%) | Viscosity (Centipoise) |
| --- | --- | --- |
| #1 | 6.5 | 5.7 |
| #2 | 6.5 | 7.4 |
| #3 | 2.0 | 34.2 |
| #4 | 1.8 | 60.1 |

II. Electrophoretic Separations

The polymers, synthesized as described above, were used to perform separations of standard nucleic acid samples in a microscale integrated channel device to demonstrate their efficacy, as follows:

A. Separation of 100 bp Ladder with Control Polymer #1

A 6.5% solution of neutral control polymer (Polymer #1) was prepared by dissolving the polymer in water at a concentration of 10% (w/v). The polymer solution for use in separations was then made up by mixing 0.65 ml of polymer solution, 0.2 ml Genetic Analysis Buffer (Perkin-Elmer, Norwalk Conn.), and 0.15 ml distilled water. Intercalating dye (Syto 61, Molecular Probes, Inc.) was added to the polymer solutions at a ratio of 1:2500. Sample buffer was prepared by adding 2 ml Genetic Analysis Buffer to 8 ml distilled water and 4 µl of Syto 61™.

Experimental separations were performed on a 100 bp ladder (Promega) which contains nucleic acid fragments ranging from 100 to 1000 bp in length, at 100 bp increments, and also including a 1500 bp fragment. The samples were prepared by diluting the stock ladder solution 1:10 in the sample buffer containing Syto 61™.

Sample separations were performed in a multi-sample microscale capillary electrophoresis device in which multiple samples are serially separated along a common separation capillary channel. The device employed a planar glass chip construction, where the channels were etched as grooves in a first planar glass substrate and a second glass substrate is overlaid and bonded to the first, to define the channels. The integrated channel device had the channel geometry shown in FIG. 1, which allows the serial analysis of up to 12 samples along the same separation channel.

The channels of the device were filled with Polymer #1 by introducing the polymer into one common reservoir and allowing the polymer solution to wick into all of the interconnected channels. Nine sample wells in the device were filled with the sample buffer containing the ladder DNA, while three wells were filled with plain sample buffer (no DNA). The separation was run in the device using an electrical controller operating under current control. Separated species were fluoresced using a red laser diode directed at a point along the separation channel, and fluoresced light was collected by an objective lens and transmitted to a photomultiplier tube for detection. Signal was recorded on a PC as a function of retention time. The separation data obtained using the neutral polymer solution, e.g., uncharged polydimethylacrylamide polymer solution, is shown in FIG. 2, as a plot of fluorescence intensity (in arbitrary units) as a function of retention time (seconds) Specifically, FIG. 2 illustrates separation of the 100 bp ladder, in three replicate separations (Sample B1, B3 and B4) as well as a control run in which no DNA was introduced (Sample B2). A total of nine replicate separations and three control runs were performed, and the data from each separation was virtually identical to that shown in FIG. 2.

B. Separation of 100 bp Ladder with Polymer #2

A solution of negatively charged polymer (Polymer #2) was prepared in the same fashion as Polymer #1, in Example II.A. above. This polymer solution was again used to perform a separation of an identically prepared nucleic acid sample in an identical multi-sample device under identical electrical control.

FIG. 3 illustrates the data obtained using Polymer #2 in the identical separation (Sample B1, B3 and B4) and control (Sample B2). Again, a total of ten replicate separations and two control runs were performed, and the data in each case was virtually identical to that shown.

C. Separation of a 100 bp Ladder with Polymer #3

Figure 4:
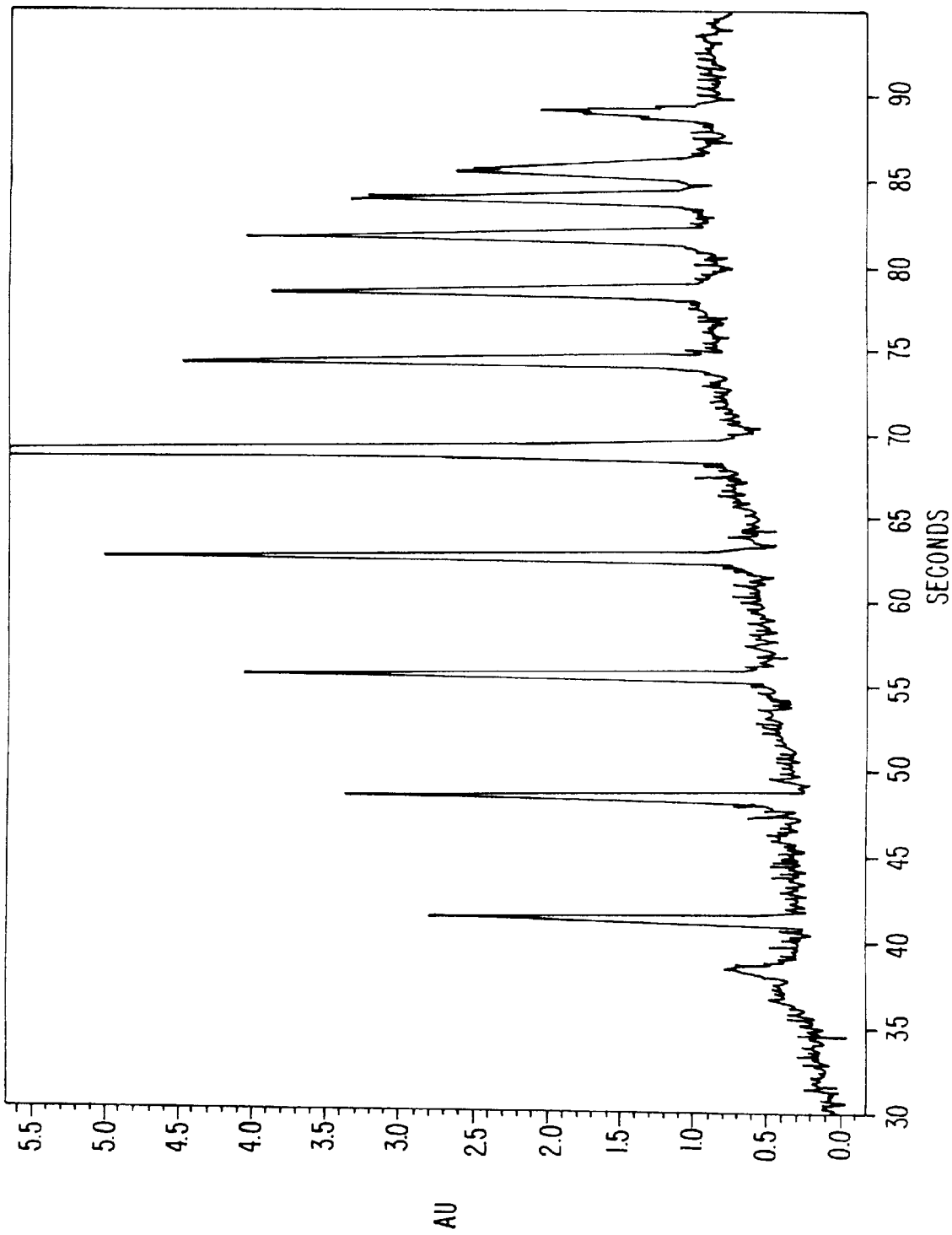
FIG. 4 illustrates a chromatographic separation as in FIG. 3, but employing a charged polymer that has a larger average molecular weight and viscosity than the polymer solution used in generating the chromatogram shown in FIG. 3.

A 2.0% solution of Polymer 3 was prepared by adding 0.20 g of Polymer 3, 2.0 g of Genetic Analysis Buffer and 7.80 g of water to a 20 ml glass vial. The mixture was stirred for one hour then passed through a 0.2 micron filter. Intercalating dye (Syto 61, Molecular Probes, Eugene Oreg.) was added to the solution at a 1:2500 ratio. Sample buffer was prepared by adding 2 ml of Gene Scan buffer to 8 ml of deionized water and 4 $\mu$l of Syto 61. Separation of the 100 bp ladder was again carried out under conditions and using systems identical to that described above. A representative separation is shown in FIG. 4. As can be seen from FIG. 4, all 11 fragments of the ladder were separated in less than 90 seconds.

D. Separation of a 100 bp Ladder with Polymer #4

Figure 5:
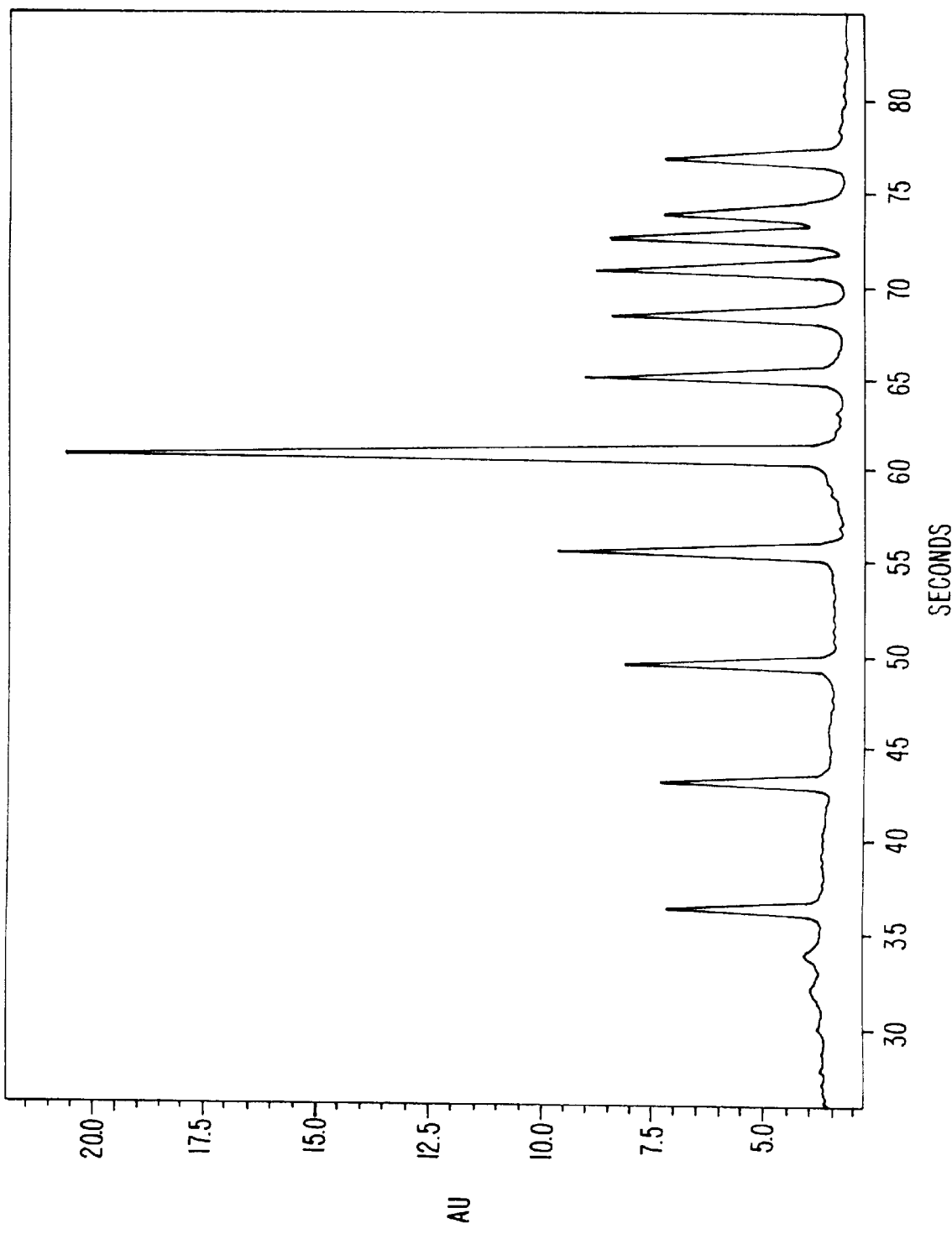
FIG. 5 illustrates a chromatographic separation as in FIG. 4, except employing a polymer solution that has a still larger molecular weight and viscosity than the polymer used in generating the chromatogram shown in FIG. 4.

A 1.8% solution of Polymer 4 was prepared by adding 0.18 g of Polymer 4, 2.0 g of Genetic Analysis Buffer and 7.82 g of water to a 20 ml glass vial. The mixture was stirred for one hour then passed through a 0.2 micron filter. Intercalating dye (Syto 61, Molecular Probes, Eugene Oreg.) was added to the solution at a 1:2500 ratio. Sample buffer was prepared by adding 2 ml of Gene Scan buffer to 8 ml of deionized water and 4 $\mu$l of Syto 61. Again, a representative separation using Polymer #4 is shown in FIG. 5, wherein all 11 fragments are again clearly resolved in less than 90 seconds.

As can be seen from the foregoing examples, the negatively charged polymer solutions (Polymers #2, #3, and #4) provide very high-resolution separation of the nucleic acid fragments in repeated runs. These separations were on par with, and in some cases, better than the separations obtained using neutral polymer solutions (Polymer #1).

E. Comparison of Electroosmotic Flow in Neutral and Negatively Charged Polymer Solutions The level of electroosmotic flow was also determined for the neutral and charged polymer solutions (Polymers #1 and #2, respectively). The same protocol described above was used for this measurement, with the exception that Rhodamine B, a neutral fluorescent indicator of electroosmotic flow, was added to the sample buffer at 1 $\mu$M concentration, in place of the 100 bp ladder. A field of 350 mV/cm was applied to the sample well containing the Rhodamine B and its progression was visually monitored on a fluorescent detection microscope. An electroosmotic flow of $8.0 \times 10^{-6}$ cm$^2$V$^{-1}$s$^{-1}$ was measured for the neutral, uncharged polymer solution, while an electroosmotic flow rate of $4.2 \times 10^{-6}$ cm$^2$V$^{-1}$s$^{-1}$ was measured for the negatively charged polymer solution. Thus, in addition to providing a more than adequate reduction in electroosmotic flow, the negatively charged polymer surprisingly caused a greater reduction in that flow over neutrally charged polymer in the experiment performed. In any event, both values represent an approximate 20-fold reduction in electroosmotic flow over uncoated silica capillaries.

F. Macromolecular Separations in Planar Polymeric Substrates

1. Fabrication of a Plastic Planar Capillary Structure

Figure 6:
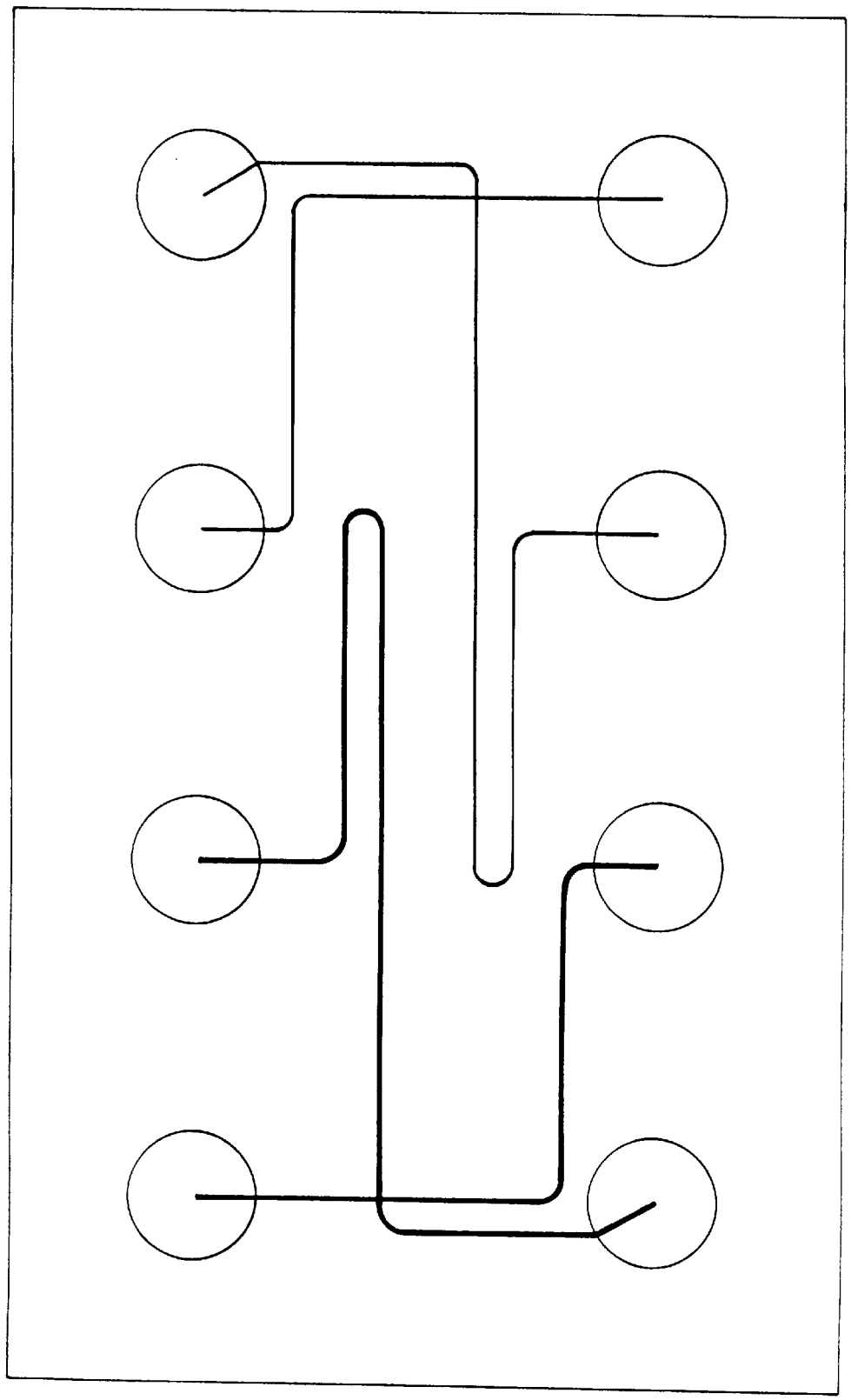
FIG. 6 illustrates a channel geometry for a planar polymeric substrate/microscale channel device used to perform macromolecular separations in accordance with the present invention.

The layout of the planar capillary structure is found in FIG. 6. The first fabrication step was to laser ablate the capillaries into a 0.2×3.7×2.2 cm piece of cast polymethylmethacrylate with an eximer laser to create a channel plate. The laser-ablated channels were measured at 12.5 microns deep and 85 microns wide. A top plate with the same exterior dimensions as the channel plate but having 0.25-cm holes drilled through it that aligned with where the channels terminate on the channel plate was also fabricated. The two plates were sandwiched together and then bonded by applying 10 kilograms of weight and then heating the assembly to 92C for two hours. The weight was then removed and the part was cooled to ambient temperature.

2. Suppression of Electroosmotic Flow by Polymer #3 in a Plastic Planar Capillary The electroosmotic flow of the structure was measured first with buffer as a control. Genetic Analysis Buffer (Perkin-Elmer) was used for the measurement. It was prepared by mixing 1 ml of the 10X buffer concentrate with 9 ml of deionized water. A neutral dye, Bodipy-Fluorescein (Molecular Probes) was added to an aliquot of the buffer to serve as an electroosmotic flow marker. The plastic capillary structure was first filled with the buffer solution. One of the wells was then filled with the buffer containing the neutral dye. The structure was run on the microscope system described in Example E and the migration of the dye was followed visually. The electroosmotic flow was measured at $2.26 \times 10^{-4}$ cm$^2$/sec-V.

The electroosmotic flow was then measured with a 2.0% solution of Polymer #3 in Genetic Analysis Buffer. This solution was prepared as described above with the exception that Syto 61 was not added. The polymeric substrate previously described was filled with the polymer solution. One well was filled with the Bodipy Fluorescein buffer solution. The field was applied and the rate of migration of the dye was measured visually. The field was then reversed and the migration of the dye was measured visually. With the field reversed the dye migrated at the same rate in the opposite direction. The electroosmotic flow was calculated to be $2.54 \times 10^{-6}$ cm$^2$/sec-V, a factor of 20 lower then in the buffer control.

Figure 7:
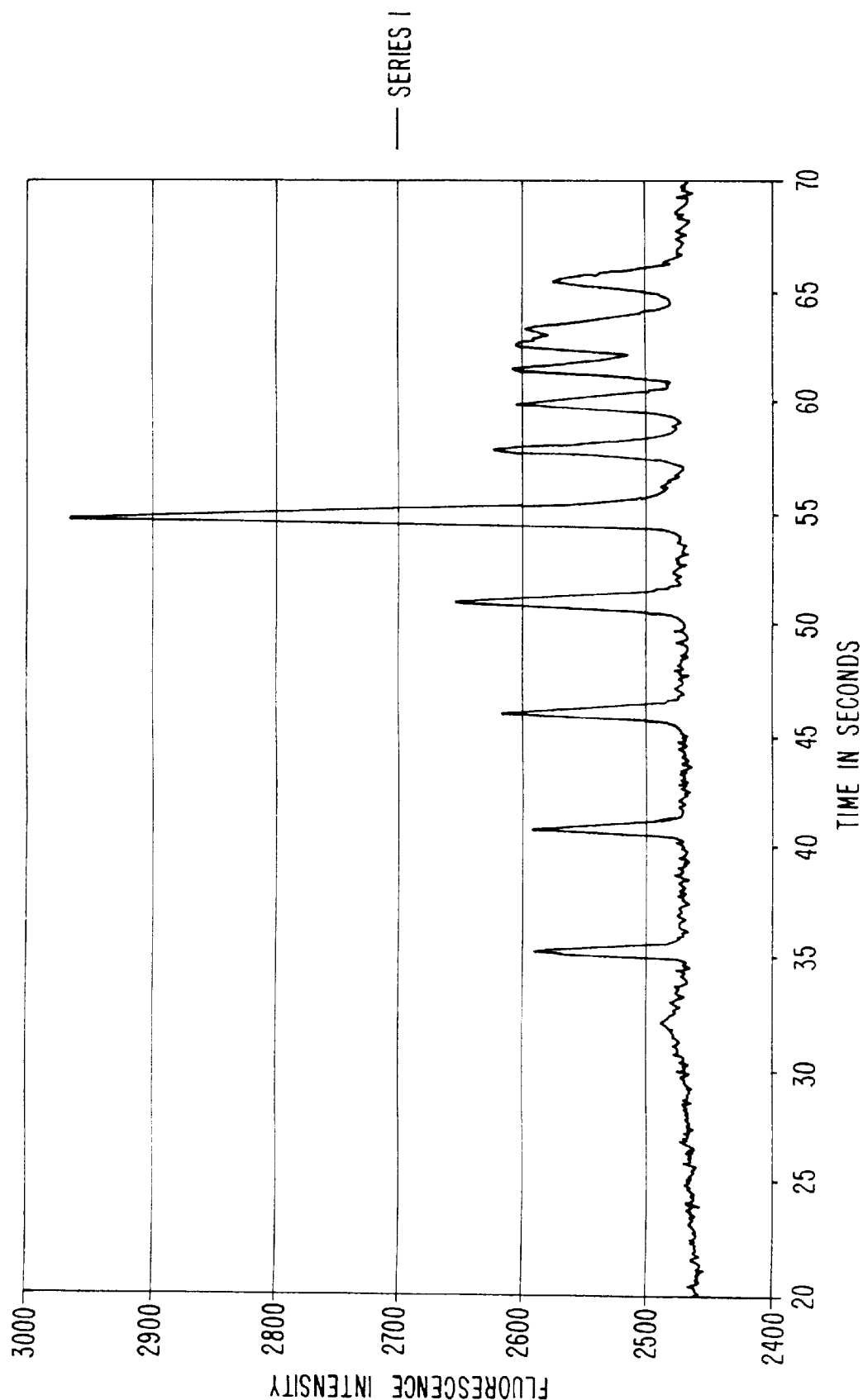
FIG. 7 illustrates a chromatographic separation of a 100 bp ladder in a polymethylmethacrylate microfluidic device using a polymer of the invention.

3. DNA Separations in a Polymeric Device Using Polymer #3 as a Separation Matrix All buffers and DNA samples were prepared as described above. The microscale channel device used was described in F1, above. The device was run on a fluorescent detection microscope system equipped with a 3 mW red solid state laser (Coherent). The field applied was 210 v/cm with a separation length of 1.8 cm from injection to detection point. The separation is illustrated in FIG. 7 from which it can be seen that the 11 fragments in the ladder are distinguishable.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of separating macromolecules by capillary electrophoresis, comprising:
   providing a substrate comprising at least a first capillary channel disposed therein, a surface of the channel having a first surface charge associated therewith;
   filling said capillary channel with a water soluble hydrophilic polymer solution having a percent charge of from about 0.01% to about 2%, as calculated by the molar percent of charged monomer subunits to total monomer utilized in producing the polymer, the charged monomer subunits consist of monomer subunits having a charge that is the same as the first surface charge;
   introducing a sample containing the macromolecules into one end of the capillary channel and;
   applying a voltage gradient across the length of the capillary channel, whereby the macromolecules in the sample are separated in the capillary channel.

2. The method of claim 1, wherein the substrate provided in the providing step comprises a first surface charge that is negative, and the charged monomer subunits in the filling step consist of negatively charged monomer subunits.

3. The method of claim 2, wherein the negatively charged monomer units are selected from acrylic acid, bisacrylamidoacetic acid, 4,4-Bis(4-hydroxyphenyl)pentanoic acid, 3-butene-1,2,3-tricarboxylic acid, 2-carboxyethylacrylate, itaconic acid, methacrylic acid, 4-vinylbenzoic acid, sulfonic acid, 2-acrylamido-2-methyl-1-propanesulfonic acid, 2-methyl-2-propene-1-sulfonic acid, 2-propene-1-sulfonic acid, 4-styrenesulfonic acid, 2-sulfoethyl methacrylate, 3-sulfopropyldimethyl-3-methacrylamidopropylammonium inner salt, 3-sulfopropyl methacrylate, vinylsulfonic acid, Bis(2-methacryloxyethyl)phosphate, and monoacryloxyethyl phosphate.

4. The method of claim 1, wherein the substrate provided in the providing step is a silica-based substrate.

5. The method of claim 4, wherein the substrate provided in the providing step comprises a silica substrate, and the polymer in the filling step comprises polydimethylacrylamide-co-acrylic acid.

6. The method of claim 1, wherein the substrate provided in the providing step comprises a solid polymeric substrate.

7. The method of claim 6, wherein the solid polymeric substrate is selected from the group of polydimethylsiloxanes (PDMS), polymethylmethacrylate (PMMA), polyurethane, polyvinylchloride (PVC), polystyrene, polysulfone, polycarbonate, polytetrafluoroethylene.

8. The method of claim 1, wherein the sample contains a plurality of different nucleic acid sequences.

9. The method of claim 8, wherein the different nucleic acids comprise a plurality of different fragments of a target nucleic acid sequence.

10. The method of claim 9, wherein the different nucleic acids comprise a nested set of fragments of a target nucleic acid sequence.

11. The method of claim 10, wherein the each fragment in the nested set of fragments differs from at least one other fragment in the nested set by the addition or omission of a single nucleotide at a terminus of the fragment.

12. The method of claim 1, wherein the capillary channel provided in the providing step intersects and is fluidly connected with at least a second capillary channel disposed in the substrate.

13. The method of claim 1, wherein the capillary channel provided in the providing step intersects and is fluidly connected with at least second and third capillary channels disposed in the substrate.

14. The method of claim 13, wherein the applying step comprises simultaneously applying a voltage gradient across each of the first and second capillary channels, to transport the sample from the second channel into the first channel and to separate macromolecules in the sample in the first channel.

15. The method of claim 13, wherein the applying step comprises simultaneously applying a voltage gradient across each of the first, second and third capillary channels.

16. The method of claim 1, wherein the polymer in the polymer solution has a net charge of between about 0.01% and 1%.

17. The method of claim 1, wherein the polymer in the polymer solution has a net charge of between about 0.01% and 0.5%.

18. The method of claim 1, wherein the polymer in the polymer solution has a net charge of between about 0.05% and 0.2%.

19. The method of claim 1, wherein the polymer solution comprises a polymer concentration of between about 0.01% and about 20% (w/v).

20. The method of claim 1, wherein the polymer solution comprises a polymer concentration of between about 0.1% and about 10% (w/v).

21. The method of claim 1, wherein the polymer solution has a viscosity of between about 2 centipoise and about 1000 centipoise.

22. The method of claim 1, wherein the polymer solution has a viscosity in a range of from about 5 centipoise to about 200 centipoise.

23. The method of claim 1, wherein the polymer solution comprises a viscosity in a range of from about 10 centipoise to about 100 centipoise.

24. The method of claim 1, wherein the polymer comprises a molecular weight from about 1 Kd, to about 5,000 Kd.

25. The method of claim 1, wherein the polymer is a polydimethylacrylamide polymer and the charged monomer is acrylic acid.

26. A method of separating macromolecules by capillary electrophoresis, comprising:
   providing a silica substrate having a capillary channel disposed therein, a surface of the channel having a negative surface charge associated therewith;
   filling said capillary channel with a water soluble hydrophilic polymer solution having a net charge of from about 0.1% to about 2%, the charge being the same as the surface charge;
   introducing a sample containing the macromolecules into one end of the capillary channel; and
   applying a voltage gradient across the length of the capillary channel, whereby the macromolecules in the sample are separated in the capillary channel.

27. A method of preparing a walled capillary channel for use in separating macromolecules, comprising:

filling the capillary channel with a silica adsorbing polymer solution, wherein the polymer has a net charge that is the same as a net charge associated with interior surfaces of the walled capillary channel.

28. A system for separating macromolecules by capillary electrophoresis, comprising:

a substrate having at least a first walled capillary channel disposed therein, the channel having a net surface charge associated with interior surfaces of the channel;

a solution of silica adsorbing polymer disposed in the capillary channel, the solution of polymer comprising:
a molecular weight between about 1 Kd and 5,000 Kd;
a net charge of between about 0.01 and 2%, the net charge being the same as the net surface charge; and a power source electrically coupled to the first capillary channel for applying a voltage gradient across the capillary channel.

29. The system of claim 28, wherein the net surface charge associated with the interior surfaces of the capillary channel is negative.

30. The system of claim 29, wherein the substrate is a silica substrate.

31. The system of claim 30, wherein the substrate is selected from a silica capillary tube and an etched planar silica substrate.

32. The system of claim 28, wherein the substrate comprises a solid polymeric substrate.

33. The system of claim 32, wherein the solid polymeric substrate is selected from the group of polydimethylsiloxanes (PDMS), polymethylmethacrylate (PMMA), polyurethane, polyvinylchloride (PVC), polystyrene, polysulfone, polycarbonate, polytetrafluoroethylene.

34. The system of claim 28, wherein the substrate further comprises at least a second walled capillary channel disposed in the substrate, the second walled capillary channel intersecting and in fluid communication with the first walled capillary channel.

35. The system of claim 34, wherein the power source is electrically coupled to each of the fist and second capillary channels, the power supply simultaneously applying a voltage gradient across a length of each of the first and second capillary channels.

36. The system of claim 28, wherein the polymer has a net charge between about 0.01% and about 1%.

37. The system of claim 28, wherein the polymer has a net charge between about 0.01% and 0.5%.

38. The system of claim 28, wherein the polymer has a net charge between about 0.05% and 0.2%.

39. The system of claim 28, wherein the polymer solution comprises a polymer concentration in a range of from about 0.01% to about 20% (w/v).

40. The system of claim 28, wherein the polymer solution comprises a polymer concentration in a range of from about 0.1% to about 10% (w/v).

41. The system of claim 28, wherein the polymer solution comprises a viscosity of between about 2 centipoise and about 1000 centipoise.

42. The system of claim 28, wherein the polymer solution comprises a viscosity in a range of from about 5 centipoise to about 200 centipoise.

43. The system of claim 28, wherein the polymer solution comprises a viscosity in a range of from about 10 centipoise to about 100 centipoise.

44. The system of claim 28, wherein the polymer is an acrylic polymer and the charged monomer subunits are selected from acrylic acid, bisacrylamidoacetic acid, 4,4-Bis(4-hydroxyphenyl)pentanoic acid, 3-butene-1,2,3-tricarboxylic acid, 2-carboxyethylacrylate, itaconic acid, methacrylic acid, 4-vinylbenzoic acid, sulfonic acid, 2-acrylamido-2-methyl-1-propanesulfonic acid, 2-methyl-2-propene-1-sulfonic acid, 2-propene-1-sulfonic acid, 4-styrenesulfonic acid, 2-sulfoethyl methacrylate, 3-sulfopropyldimethyl-3-methacrylamidopropylammonium inner salt, 3-sulfopropyl methacrylate, vinylsulfonic acid, Bis(2-methacryloxyethyl)phosphate, and monoacryloxyethyl phosphate.

45. The system of claim 28, wherein the polymer comprises polydimethylacrylamide-co-acrylic acid.

46. The system of claim 28, wherein the polymer has a net negative charge.

47. The system of claim 28, wherein the polymer is made by the process of polymerizing dimethylacrylamide monomers in the presence acrylic acid, the acrylic acid being present at a concentration of between about 0.01 and 2% of a total monomer concentration.

48. The system of claim 28, wherein the first net surface charge is capable of supporting an electroosmotic mobility of a buffer comprising from about 1 mM to about 10 mM sodium borate buffer, at a pH of from about 7 to about 9, disposed in the walled capillary channel, the electroosmotic mobility being at least about $1 \times 10^{-5}$ $cm^2 V^{-1} s^{-1}$.

49. A system for separating nucleic acids by molecular weight, comprising:

a silica substrate having a walled capillary channel disposed therein, the channel having a negative charge associated with interior surfaces of the channel;

a solution of silica adsorbing polymer disposed in the capillary channel, the solution of polymer comprising:
a molecular weight between about 1 Kd and 5,000 Kd;
a net negative charge of between about 0.01 and 2%; and a power source for applying a voltage gradient across the capillary channel.

50. A walled capillary for separating macromolecules by capillary electrophoresis, comprising:

a capillary channel disposed in a solid substrate, interior surfaces of the capillary channel having a first net surface charge associated therewith; and a solution of silica adsorbing polymer disposed in the capillary channel, the polymer comprising:
a molecular weight between about 1 Kd and about 5,000 Kd;
a net charge of between about 0.01 and 2%, the net charge being the same as the first net surface charge.

* * * * *

UNITED STATES PATENT AND TRADEMARK OFFICE
CERTIFICATE OF CORRECTION

PATENT NO. : 5,948,227  
DATED : September 7, 1999  
INVENTOR(S) : Dubrow

Page 1 of 1

It is certified that error appears in the above-identified patent and that said Letters Patent is hereby corrected as shown below:

Column 4,
Line 25, please delete "184" and insert -- 188 --.

Signed and Sealed this

Fifth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 5,948,227                                    Page 1 of 1
DATED         : September 7, 1999
INVENTOR(S)   : Dubrow It is certified that error appears in the above-identified patent and that said Letters Patent is hereby corrected as shown below:

Drawings,
Sheet 1 of 9, please replace Figure 1 with the following new Figure 1.

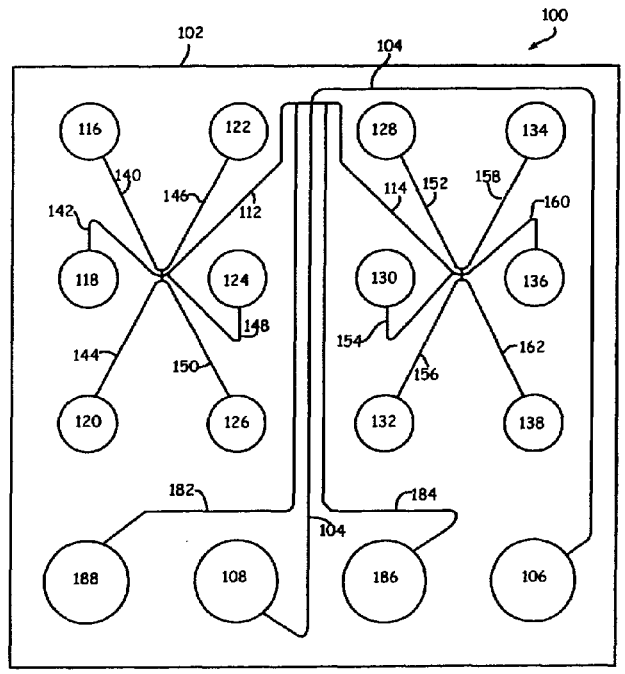

Fig. 1.

Signed and Sealed this

Twenty-sixth Day of November, 2002

*Attest:*

*Attesting Officer*

JAMES E. ROGAN
*Director of the United States Patent and Trademark Office*